United States Patent [19]

Peck et al.

[11] Patent Number: 4,880,924
[45] Date of Patent: Nov. 14, 1989

[54] NOVEL COMPOUNDS AND USE THEREOF IN SELECTIVE CYCLIZATION PROCESS

[75] Inventors: James V. Peck, Costa Mesa; Gevork Minaskanian, Irvine, both of Calif.

[73] Assignee: Nelson Research & Development Co., Irvine, Calif.

[21] Appl. No.: 847,639

[22] Filed: Apr. 3, 1986

[51] Int. Cl.$^4$ ............................................. C07D 491/06
[52] U.S. Cl. ................................... 540/520; 540/521; 546/116; 548/453
[58] Field of Search ................ 540/520, 521; 546/116; 548/453

[56] References Cited

FOREIGN PATENT DOCUMENTS 0910056 4/1954 Fed. Rep. of Germany ...... 540/521

OTHER PUBLICATIONS

Polymer Chemistry–An Introduction by Malcolm P. Stevens (Addison–Wesley) (1975), pp. 263–266.
Textbook of Polymer Science by Fred Billmeyer (Wiley–Interscience) (Third Edition) (1984), pp. 96–97.
C. G. Overberger et al., "Asymmetric Polymers, XXV, Synthesis of Some Optically Active C–Substituted Hexahydro-2H-Azepin-2-Ones", J. Polymer Sci.: Part A-1, vol. 10, 2265–2289 (1972).

*Primary Examiner*—Robert T. Bond
*Attorney, Agent, or Firm*—Robert J. Baran; June M. Bostich

[57] ABSTRACT

This invention relates to a selective process for preparing bicyclic lactam-lactone compounds wherein the rings are fused, i.e. the rings share at least two carbon atoms, or are isolated. In particular, the present invention provides a process for selectively reacting novel 1-hydrocarbylamino (or heteroatom-substituted hydrocarbylamino); 1,1-dicarboxylic acid, alkylesters; 1-alkanolactonyl or hydrocarbyl (or heteroatom-substituted hydrocarbyl) alkanonylactonyl methane, as the salt of an acid having a pKa of 0 or more, to provide bicyclic lactam-lactone compounds. The selectively of the reaction to either fused or isolated bicyclic compounds is controlled by cyclizing the novel salts, in the absence of a base, a cyclizing said novel salts, in the presence of an amount of base substantially equivalent to said acid, respectively.

14 Claims, No Drawings

NOVEL COMPOUNDS AND USE THEREOF IN SELECTIVE CYCLIZATION PROCESS

FIELD OF THE INVENTION

This invention relates to a selective process for preparing bicyclo lactam-lactone compounds wherein the rings are fused, i.e. the rings share at least two carbon atoms, or are isolated. In particular, the present invention provides a process for selectively reacting novel 1-hydrocarbylamino (or heteroatom-substituted hydrocarbylamino); 1,1-dicarboxylic acid, alkylesters; 1-alkanolactonyl or hydrocarbyl (or heteroatom-substituted hydrocarbyl) alkanonylactonyl methane, as the salt of an acid having a pKa of 0 or more, to provide bicyclic lactam-lactone compounds. The selectivity of the reaction to either fused or isolated bicyclic compounds is controlled by cyclizing the novel salts, in the absence of a base, or cyclizing said novel salts, in the presence of an amount of base substantially equivalent to said acid, respectively.

DESCRIPTION OF THE ART

Lactams are cyclic amides and lactones are cyclic esters having many uses as intermediates for the preparation of polymers, medicinals, etc. In particular, in medicinal uses, certain lactams have been found to enhance the transdermal penetration of various physiologically-active compounds into the tissues and blood stream of an animal, e.g. a human. See, for example, U.S. Pat. Nos. 3,989,816; 4,316,893; 4,310,525; 4,422,970; and 4,405,616; wherein lactams, in particular 1-n-alkyl azacycloalkan-2-ones, having a ring size of from 5 to 9 members are shown to enhance the transdermal penetration of physiologically-active materials. It has been found that both the size of the ring and the length of the n-alkyl group affects the transdermal penetration-enhancing properties of the 1-n-alkylazacycloalkan-2-ones disclosed in these patents. Thus, it would be desirable to have a process for selectively varying both the ring size and the length of the n-alkyl group. One of the 1-alkylazacycloalkan-2-ones, disclosed in the above patents, 1-n-dodecyl-azacycloheptan-2-one, has been found to be particularly effective as a transdermal penetration-enhancing vehicle. However, the water-insolubility of this compound has hindered its use with certain physiologically-active materials. One of the novel lactone-lactam compounds disclosed below may be converted into a water-soluble derivative of 1-n-dodecylazacycloheptan-2-one.

Lactams are also useful in the preparation of nylon 6-type polymers wherein the properties thereof may be systematically modified through the regulation of the nature and position of the lactam substituent. See, for example, C. G. Overberger et al., Journal of Polymer Science, Vol. 10, 2265–2289 (1972).

Also, compounds having both lactam and lactone functionality would be important, for the above industrial uses, as well as to serve as intermediates to other useful compounds, e.g. medicinals.

SUMMARY OF THE INVENTION

It has unexpectedly been found that 1-hydrocarbylamino (or heteroatom substituted hydrocarbyl amino), 1,1-dicarboxylic acid, alkyl esters, 1-alkanolactonyl or hydrocarbyl (or heteroatom-substituted hydrocarbyl) alkanol lactonyl methane, as the salt of an acid having a pKa of 0 or more, may be selectively cyclized to bicyclic lactone-lactam compounds, wherein the rings are fused, i.e. the rings share at least two carbon atoms, or are isolated, by cyclizing in the absence of a base or by first neutralizing said acid with an amount of base substantially equivalent to said acid, and then carrying out said cyclization process, respectively.

These bicyclic lactone-lactam compounds are useful as intermediates for physiologically-active compounds, as solvents for physiologically-active compounds, as intermediates for polymers, e.g. Nylon polymers, as plasticizers for polymers, etc. In particular the novel 5,7-bicyclic lactone-lactam or 6,6-bicyclic lactone-lactam compounds may be converted to 2,3'- or 2,2'-di-γ-aminobutyric acid (GABA Dimer) by successive ammonolysis to the lactam-lactam and hydrolysis in the presence of aqueous hydrochloric acid. The 5,5-lactone-lactam ester may be converted to a GABA derivative, having CNS activity, by acid hydrolysis in the presence of a strong acid, e.g. HCl. In fact, any of the 5-membered lactams may be converted to a GABA derivative which, like GABA, itself, would show CNS activity.

DESCRIPTION OF THE INVENTION

The present invention provides a process for converting a first compound, represented by the general formula:

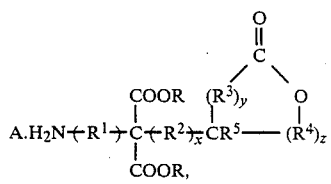

selectively, into a second compound represented by the general formula

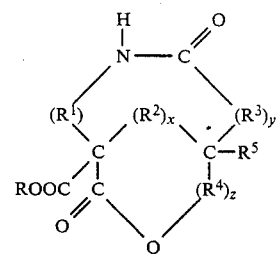

or into a second compound represented by the general formula:

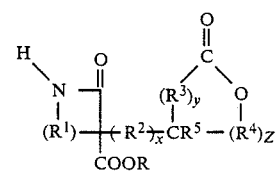

by cyclizing said first compound in the absence of a base or by neutralizing said compound with an amount of base substantially equivalent to A (A represents a weak acid, i.e. an acid having a pKa of 0 or more) and then cyclizing said first compound. Thus, either fused bicyclic lactam-lactone compounds or isolated bicyclic lactam-lactone compounds may be prepared, selectively, by carrying out the cyclization in the absence or presence of a base.

The reaction is general in nature, provided that the first compound has the structure represented by the above general formula, wherein R is an akyl radical having from one to eight carbon atoms; $R^1$ is a divalent hydrocarbyl or heteroatom-substituted hydrocarbyl radical providing at least two carbon atoms between the nitrogen atom and the 1-carbon atoms; $R^2$, $R^3$ and $R^4$ are divalent hydrocarbyl radicals) or hetero atom-substituted hydrocarbyl radicals; $R^5$ is hydrogen or a hydrocarbyl or heteroatom-substituted hydrocarbyl radical; x is 0; y and z are 0 or integers of from 1 to 3, provided at least one of y and z is not 0; and said heteroatoms are selected from the group consisting of nitrogen, oxygen, sulfur, phosphorus and halogen atoms, e.g. fluorine and chlorine atoms.

Preferably, $R^1$ comprises from two to five carbon atoms and more preferably is an alkyl, alkenyl or heteroatom substituted alkyl or alkenyl radical. In the most preferred embodiment of this invention $R^1$ is an ethylene radical.

$R^2$, $R^3$ and $R^4$ preferably comprise from two to five carbon atoms and are more preferably alkyl, alkenyl or heteroatom-substituted alkyl or alkenyl radicals. Most preferably, $R^2$, $R^3$ and $R^4$ are methylene or ethylene radicals.

$R^5$ is preferably hydrogen or an alkyl radical having from one to four carbon atoms, e.g. methyl or ethyl; more preferably $R^5$ is a hydrogen radical.

Preferably, x is 0 and y is 0 and z is 1 or z is 0 and y is 1. Thus, the butanolactonyl derivatives, wherein the lactonyl radical is covalently bound directly to the 1-carbon atom are the preferred compounds represented by the above general formula for the first compound.

A represents a weak acid, i.e. an acid having a pKa of 0 or more; preferably 1.5 or more. Suitable acids include carboxylic acids having from one to ten, more preferably from one to six carbon atoms, e.g. acetic acid and propionic acid. Halogenated carboxylic acids, e.g. fluorinated aand chlorinated carboxylic acids, such as trichloroacetic acid and trifluoroacetic acid are also suitable.

Thus, 1-ethylamino, 1,1-dicarboxylic acid, ethylesters, 1-(2-butanolactonyl) methane and 1-ethylamino; 1,1-dicarboxylic acid, ethyl esters, 1-(3-butanolactonyl) methane are selectively converted into fused bicyclic lactam-lactones or isolated bicyclic lactam-lactones, by cyclizing the first compound in the absence or presence of a base, respectively.

The base may be selected from the group consisting of Group I and II metal oxides, hydroxides and carbonates or any other compound or salt which provides a pH greater than 7 when contacted with the above-defined first compound. For example, sodium hydroxide, potassium hydroxide, sodium oxide, potassium oxide, calcium oxide, calcium hydroxide, calcium carbonate, are suitable bases for the process of the present invention.

The cyclization process is varied in accordance with the desire to obtain either fused-lactone-lactams or isolated lactone-lactams.

To obtain the fused lactone-lactams, the cyclization is effected without neutralization of the acid moiety A. This cyclization reaction is preferably carried out in an inert solvent for the first compound, e.g. a chlorinated organic solvent, such as chloroform, methylene chloride, etc., an ether, e.g. diethyl ether, tetrahydrofuran, etc. Preferably, a chlorinated organic solvent is used to dissolve the first compound, e.g. chloroform or methylene chloride.

To obtain isolated lactone-lactams the weak acid A should be neutralized with a substantially equivalent amount of a base prior to cyclization. (For the purposes of this invention, a substantially equivalent amount of base may vary from 0.8 to 1.2 equivalents per equivalent of A. Preferably, the amount of base varies from 0.9 to 1.1 per equivalent of A.) Thus, the first compound may be mixed with an aqueous solution containing an amount of base substantially equivalent to A and the resulting lactam subsequently extracted with a solvent, e.g. one of the organic solvents described above. (It should be noted that the identity of A is not limited to acids having a pKa of 0 or more, when the cyclization in the presence of a substantially equivalent amount of base is carried out to obtain isolated lactone-lactams. That is, the salts of the first compound and an acid having a pKa of less than 0, e.g. hydrochloric acid, may be neutralized with a substantially equivalent amount of base and then cyclized to an isolated lactone-lactam.)

Alternatively, to obtain isolated lactone-lactams, the first compound may be mixed with water and the resulting mixture stirred in the presence of waer-immiscible solvent for the lactam. To this two phase mixture, aqueous base may be slowly added whereby the acid is neutralized and dissolves in the water-immiscible solvent. Again, the water-immiscible solvent may be selected from the organic solvents described above, with the chlorinated solvents such as chloroform and methylene chloride being preferred.

The present process may be carried out at a temperature of from 0° to 150° C.; preferably from 25° to 35° C., and most preferably about 0° C. The pressure is not critical and may vary from 1 to 10 atmospheres; preferably from 1 to 5 atmospheres. (To obtain the fused lactone-lactam, cyclization at a temperature of from 20° C. to 50° C. is most preferred. To obtain the isolated lactone-lactams cyclization at a temperature of about 0° C. is preferred.) When the above-defined first compound is prepared as a salt of an acid, e.g. the acetate, it is important to immediately carry out the base-catalyzed reaction if high selectivity to the resulting base catalyzed product is desired. For example, when the freshly-prepared acetate salt of 1-(3-butanolactonyl), 1,1 dicarboxylic acid, diethyl ester, 1-aminomethyl-methane is immediately neutralized with sodium hydroxide, a selectivity to the isolated lactone-lactam of 91 percent is obtained. However, stirring the unneutralized salt overnight provides the fused lactone-lactam at a selectivity of 96 percent, demonstrating that, when thermodynamically favorable, the first compound will cyclize to the fused ring lactone-lactam with time.

The invention is further illustrated by the following examples which are illustrative of various aspects of the invention, and are not intended as limiting the scope of the invention as defined by the appended claims.

EXAMPLE 1

Preparation of (Cyanomethyl)(tetrahydro-5-oxo-3-furanyl)propanedioic acid diethyl ester A flame-dried flask was charged with a stirred suspension of 1.0 g (0.02 mmol) of NaH (50% dispersion in mineral oil; washed free of oil with 2×20 mL portions of dry pet ether) in 150 mL dry THF under argon at 0° C. To the suspension, 41.2 g (0.20 mol) of ethyl 2-carboethoxy-3-cyano propionate was added dropwise (60 min) and the clear solution stirred for an additional 15 min at 0° C. A solution of 21.0 g (0.25 mol) of freshly distilled crotonolactone in 20 mL dry THF was added dropwise under a period of 30 min. After the addition was complete, the flask was sealed tightly under argon and stirred at 5° C. for 3 days. Water (50 mL) was added and the product extracted with 2×100 mL portions of chloroform. The organic extracts were combined, washed with water, saturated sodium chloride, dried over anhydrous magnesium sulfate, and evaporated under vacuum. The resultant crude white solid was triturated in cold ether and filtered to give 53 g (93%) of the named compound suitable for use in subsequent reactions. It was further purified for analysis by recrystallization in ethyl acetate/ether to give white crystals, mp 77°–78° C.

Anal. Calcd, for $C_{13}H_{17}NO_6$: C, 55.12; H, 6.05; N, 4.94. Found: C, 55.27; H,, 6.11; N, 4.99.

EXAMPLE 2

Preparation of 1-(3-butanolactonyl),.1,1, dicarboxylic acid, ethyl esters 1-aminomethyl-methane To a solution of 20.0 g (0.07 mol) of the compound prepared in Example 1 in 150 mL of glacial acetic acid was added 1.0 g of platinum (IV) oxide, and the suspension was vigorously agitated under hydrogen (60 psi). Hydrogen uptake was complete in 5 to 6 h. The mixture was filtered through celite and acetic acid was removed under reduced pressure (ca. 0.5 mm) at 30°–35° C. To the ice-cold oily residue was added 100 mL of cold water followed by 50 mL of chloroform. The aqueous phase was neutralized (pH 7 to 8) by dropwise addition of 1N aqueous sodium hydroxide (while shaking) and the mixture was extracted with 2×100 mL portions of chloroform. The organic extracts were combined, dried over $MgSO_4$, and concentrated in vacuo to give a white solid. GC analysis of the solid showed 91% of 5,5-lactone-lactam-ester with a retention time of 7.26 min. Upon recrystallization from ethyl acetate/chloroform, a total of 11.0 g (65%) of compound was obtained as white crystals, as a 2:1 mixture of two diastereomers: mp 119°–122° C.; IR ($CHCl_3$) 1785, 1740, 1715 cm$^{-1}$.

Two diastereomers were separated further by MPLC (Silica, 9:1 EtOAc/pet ether) to result in white crystals.

Anal. Calcd. for $C_{11}H_{15}NO_5$: C, 54.77; H, 6.27; N, 5.80. Found: C, 54.69; H, 6.37; N, 5.75.

EXAMPLE 3

Preparation of Hexahydro-3,7-dioxo-1H-furo[3,4-d]azepine-3a(3H)-carboxylic acid ethyl ester A solution of 20.0 g (0.07 mol) of the compound prepared in Example 1 was hydrogenated and worked up as described previously. To the oily residue (containing a trace amount of acetic acid) was added 50 mL of chloroform, and the solution was stirred at room temperature overnight. The solvent was removed in vacuo and the remaining solid was triturated in pet ether and filtered. After drying under high vacuum, 15.7 g of a white solid was obtained. Analysis by gas chromatography showed 96% of 5,7-lactone-lactam-ester with a retention time of 6.76. Upon recrystallization from ethyl acetate, pure 5,7-lactone-lactam was obtained as white crystals: mp 137°–138° C.

Anal. Calcd. for $C_{11}H_{15}NO_5$: C, 54.76; H, 6.26; N, 5.80. Found: C, 54.75; H, 6.24; N, 5.76.

EXAMPLE 4

Preparation of α-(2-aminoethyl)tetrahydro-5-oxo-3-furan acetic acid

Analytically pure 5,5-ester from Example 2 was refluxed with 6N HCl and the reaction mixture was monitored by TLC (Fixion-50×8, pH 5.25). Upon completion of the reaction, a TLC of the acidic solution showed one major ninhydrin positive spot at $R_f=0.37$. The excess HCl was then removed under reduced pressure and the residue was dried under high vacuum for 48 hr. This resulted in the product as an extremely hygroscopic white solid:

Anal. Calcd. for $C_8H_{14}NO_4Cl$: C, 42.96; H, 6.31; N, 6.26. Found: C, 42.74; H, 6.30; N, 6.08.

The novel compound prepared above was investigated for its potency in interaction with GABA receptor sites in BRAIN. As described in detail in Roberts et. al. J. Neuroscience, Vol. 1, No. 2, pp. 132–140 (1981), two experiments were performed: (1) the potency of the compound in displacing $^3$H-muscimol, a known GABA agonist, from specific GABA receptor sites in mouse brain membranes, and (2) the potency in displacing $^3$H-GABA from sodium-dependent GABA binding sites in mouse brain membranes, which reflects potency for the GABA reuptake inactivation process. Concentrations of the test compound showing 50% inhibition of labelled ligand binding were: (1) $2.1 \times 10^{-6}$M and (2) $2.5 \times 10^{-5}$M. This reflects very good potency for the compound prepared in Example 4.

EXAMPLE 5

Preparation of (Cyanomethyl)(tetrahydro-5-oxo-4-furanyl)propanedioic acid diethyl ester A flame-dried flask was charged with a suspension of 500 mg (0.01 mol) of NaH (50% dispersion in mineral oil; washed free of oil with 2×20 mL portions of dry pet ether) in 20 mL dry THF under nitrogen at 0° C. To the stirred suspension, 2.07 g (0.01 mol) of ethyl 2-carboethoxy-3-cyano propionate was added dropwise and the clear solution stirred for an additional 15 min at 0° C. A solution of 0.86 mL (0.01 mol) of α-bromo-γ-butyrolactone in 10 mL dry THF was added dropwise and the mixture was refluxed overnight. Water (10 mL) was added and the product extracted with 2×100 mL portions of chloroform. The organic extracts were combined, washed with water, saturated sodium chloride, dried over anhydrous magnesium sulfate, and concentrated in vacuo. The residue was subjected to flash chromatography (silica, 1:1 ether/pet ether) and the isolated product ws Kugelrohr distilled to give 2.0 g (71%) of clear oil: bp 160°–165° C. (0.1 mm).

Anal. Calcd. for $C_{13}H_{17}NO_6$: C, 55.12; H, 6.05; N, 4.94. Found: C, 54.95; H, 6.01; N, 4.90.

EXAMPLE 6

3-(2-Hydroxyethyl)-2-oxo-4,4-piperidinedicarboxylic acid diethyl ester

To a solution of 4.35 g (0.015 mol) of the cyanodiester from Example 5 in 100 mL of glacial acetic acid was added 150 mg of platinum (IV) oxide, and the mixture was agitated under hydrogen (60 psi) until hydrogen uptake had ceased. The mixture was filtered and the acetic acid was removed under reduced pressure (Ca. 0.5 mm) at 30°–35° C. To the oily residue (containing a trace amount of acetic acid) was added 300 mL of chloroform and the mixture was stirred at room temperature for 48 h. The solvent was removed in vacuo and the residue was triturated in pet ether and filtered. The resultant solid was subjected to flash chromatography (silica, 9:1 EtOAc/MeOH). The major isolated compound was recrystallized in CHCl$_3$/hexane to give 3.54 g (80%) of white solid: mp 120°–121° C.

Anal. Calcd. for C$_{13}$H$_{21}$NO$_6$: C, 54.35; H, 7..37; N, 4.87. Found: C, 54.55; H, 7.47; N, 4.95.

EXAMPLE 7

Preparation of 2-Oxo-3-(tetrahydro-5-oxo-4-furanyl)-3-pyrrolidinecarboxylic acid ethyl ester The minor product from the previous experiment was isolated as white solid: mp 124°–137° C. (6:4 mixture of two diastereomers).

Anal. Calcd. for C$_{11}$H$_{15}$NO$_5$: C, 54.77; H, 6.27; N, 5.80. Found: C, 55.02; H, 6.14; N, 5.96.

EXAMPLE 8

Preparation of Hexahydro-1,5-dioxo-1H-pyrano[4,3-C]pyridine-8a (3H)-carboxylic acid ethyl ester A solution of 3.0 g (0.01 mol) of the hydroxy-lactam-diester from Example 6, 120 mL of ethanol, and 10.0 mL of aqueous 1N sodium hydroxide was stirred overnight at room temperature. Solvents were removed in vacuo and to the residue was added 15 mL of water. The solution was cooled in an ice-bath, acidified with 10% HCl to pH 2, followed by removal of water and excess HCl in vacuo.

The residue was subjected to flash chromatography (silica, EtOAc) to give 1.2 g (50%) of a white solid; mp 119°–120° C.

Anal. Calcd. for C$_{11}$H$_{15}$NO$_5$: C, 54.77; H, 6.27; N, 5.81. Found: C, 54.83; H, 6.26; N, 5.76.

While particular embodiments of the invention have been described it will be understood of course that the invention is not limited thereto since many obvious modifications can be made and it is intended to include within this invention any such modifications as will fall within the scope of the appended claims.

What is claimed is:

1. A process for converting a first compound, represented by the general formula:

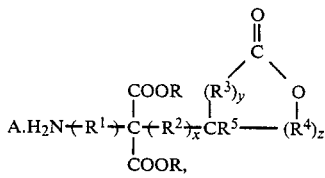

selectively, into a second compound represented by the general formula

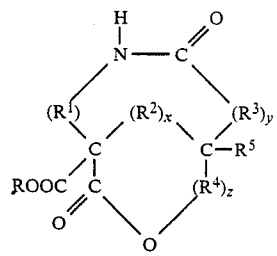

wherein R is an alkyl radical having from one to eight carbon atoms; R$^1$ is a divalent hydrocarbyl or heteroatom-substituted hydrocarbyl radical providing at least two carbon atoms between the nitrogen atom and the 1-carbon atom; R$^2$, R$^3$ and R$^4$ are divalent hydrocarbyl or heteroatom-substituted hydrocarbyl radicals; R$^5$ is hydrogen or a hydrocarbyl or heteroatom-substituted hydrocarbyl radical; A is an acid having a pKa of 0 or more; x is 0; y and z are 0 or 1, provided at least one of y and z is not 0, and said heteroatoms are selected from the group consisting of nitrogen, oxygen, sulfur, phosphorus and halogen atoms, which comprises cyclizing said first compound in the absence of a base.

2. The process of claim 1 wherein R$^1$ comprises from two to five carbon atoms and is an alkyl, alkenyl or heteroatom-substituted alkyl or alkenyl radical.

3. The process of claim 1 wherein R$^2$, R$^3$ and R$^4$ comprise from two to five carbon atoms and are alkyl, alkenyl or heteroatom-substituted alkyl or alkenyl radicals.

4. The process of claim 1 wherein R$^2$, R$^3$ and R$^4$ are selected from the group consisting of methylene or ethylene radicals.

5. The process of claim 1 wherein x is 0.

6. The process of claim 5 wherein y is 0 and z is 1 or z is 0 and y is 1.

7. The process of claim 6 wherein R$^5$ is hydrogen.

8. The process of claim 6 wherein R$^1$ is ethylene.

9. The process of claim 8 wherein R is ethyl.

10. The process of claim 9 wherein R$^3$ and R$^4$ are methylene.

11. A novel compound, 5,7-bicyclic lactone-lactam produced by the process of claim 1.

12. A novel compound, 6,6-bicyclic lactone-lactam produced by the process of claim 1.

13. A method for controlling the ring size of a lactam compound by adjusting the pH of the reaction medium, said medium consisting essentially of (1) adding to an inert solvent having an absence of base an acid salt having the formula:

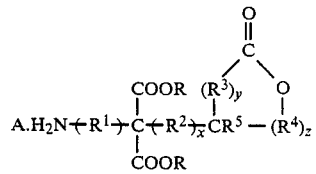

wherein R is an alkyl radical having from one to eight carbon atoms; R$^1$ is a divalent hydrocarbyl or heteroatom-substituted hydrocarbyl radical providing at least two carbon atoms between the nitrogen atom and the 1-carbon atom; R$^2$, R$^3$ and R$^4$ are divalent hydrocarbyl or heteroatom-substituted hydrocarbyl radicals; R$^5$ is hydrogen or a hydrocarbyl or heteroatom-substituted hydrocarbyl radical; A is an acid having a pKa of 0 or more; x is 0; y and z are 0 or 1, provided at least one of y or z is not 0, and said heteroatoms are selected from the group consisting of nitrogen, oxygen, sulfur, phosphorus and halogen atoms, (2) adjusting the reaction conditions so as to cause cyclization of the acid salt, and (3) recovering a fused ring lactam compound having the formula:

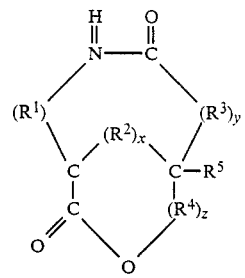

wherein $R^1$, $R^2$, $R^3$, $R^4$, x, y, and z are as defined above.

14. The method of claim 13 wherein the inert solvent is selected from the group consisting of chloroform, methylene chloride, diethyl ether, and tetrahydrofuran.

* * * * *